US012642678B2

(12) United States Patent
Rivlin et al.

(10) Patent No.: US 12,642,678 B2
(45) Date of Patent: Jun. 2, 2026

(54) 3D SUBTRACTIVE MANUFACTURING OF CASTS, BRACES, SPLINTS AND OTHER ORTHOSES

(71) Applicant: Dimension Ortho Inc., Philadelphia, PA (US)

(72) Inventors: Michael Rivlin, Philadelphia, PA (US); Pedro K. Beredjiklian, Philadelphia, PA (US); Ashkan Sedigh, Philadelphia, PA (US); Alexander R. Vaccaro, Philadelphia, PA (US); Michael J. Sileski, Philadelphia, PA (US); Steve Stubitz, Philadelphia, PA (US)

(73) Assignee: DIMENSION ORTHOTICS, LLC, Philadelphia, PA (US)

( * ) Notice: Subject to any disclaimer, the term of this patent is extended or adjusted under 35 U.S.C. 154(b) by 25 days.

(21) Appl. No.: 18/876,900

(22) PCT Filed: Jun. 21, 2023

(86) PCT No.: PCT/US2023/025802
§ 371 (c)(1),
(2) Date: Dec. 19, 2024

(87) PCT Pub. No.: WO2023/249977
PCT Pub. Date: Dec. 28, 2023

(65) Prior Publication Data
US 2025/0262077 A1       Aug. 21, 2025

Related U.S. Application Data

(60) Provisional application No. 63/353,929, filed on Jun. 21, 2022.

(51) Int. Cl.
*A61F 5/01*       (2006.01)
*A61B 5/00*       (2006.01)
*A61F 2/50*       (2006.01)

(52) U.S. Cl.
CPC .............. *A61F 5/01* (2013.01); *A61B 5/0064* (2013.01); *A61F 2/5046* (2013.01); *A61F 2002/505* (2013.01)

(58) Field of Classification Search
CPC .... A61F 5/01; A61F 2/5046; A61F 2002/505; A61B 5/0064
See application file for complete search history.

(56) References Cited

U.S. PATENT DOCUMENTS

2004/0260220 A1* 12/2004  Wagner ................. A61F 5/0127
                                                                    602/27
2005/0288809 A1* 12/2005  Spaeth ............... G05B 19/4099
                                                                    700/118
(Continued)

FOREIGN PATENT DOCUMENTS

WO          2001017467 A1      3/2001
WO          2021202433 A1      10/2021

*Primary Examiner* — Kidest Worku
(74) *Attorney, Agent, or Firm* — Panitch Schwarze Belisario & Nadel LLP

(57) ABSTRACT

A three-dimensional subtractive manufacturing system configured for constructing an orthopedic orthosis from a first blank of a plurality of blanks includes a scanner configured to capture a 3D model of a body part of a patient, a central processor configured to receive the 3D model and select the first blank based on the three-dimensional model and a computer numerical control machine configured to receive the computer numeric control programming file and an identification of the first blank from the central processor. The central processor is configured to convert the 3D model into a CNC programming file. The CNC machine comprised of a subtractive manufacturing machine. The CNC machine configured to remove material from the first blank to form the orthopedic orthosis.

12 Claims, 9 Drawing Sheets

(56)  References Cited

U.S. PATENT DOCUMENTS

| | | | | |
|---|---|---|---|---|
| 2009/0023112 | A1* | 1/2009 | Ganley | A61C 13/0022 |
| | | | | 409/117 |
| 2011/0266265 | A1 | 11/2011 | Lang | |
| 2014/0250677 | A1* | 9/2014 | Lang | A61F 2/28 |
| | | | | 29/592 |
| 2017/0071744 | A1 | 3/2017 | Bali et al. | |
| 2017/0196499 | A1* | 7/2017 | Hunter | G16H 15/00 |
| 2018/0028390 | A1* | 2/2018 | Dietl | A61F 2/50 |
| 2020/0100947 | A1 | 4/2020 | Moon | |
| 2020/0197212 | A1* | 6/2020 | Carlson | G16H 30/20 |

* cited by examiner

300

301

302

303

3D SUBTRACTIVE MANUFACTURING OF CASTS, BRACES, SPLINTS AND OTHER ORTHOSES

CROSS-REFERENCE TO RELATED APPLICATION

The present application is a U.S. national phase application under Section 371 of International Patent Application No. PCT/US23/25802, filed Jun. 21, 2023 and titled, "3D Subtractive Manufacturing of Casts, Braces, Splints and Other Orthoses," and claims the benefit of U.S. Provisional Patent Application No. 63/353,929, filed on Jun. 21, 2022 and titled "3D Subtractive Manufacturing of Casts, Braces, Splints and other Orthoses," the entire contents of which are incorporated herein by reference in their entirety.

BACKGROUND OF THE INVENTION

Three-dimensional ("3D") scanners are widely used in different industries such as additive and subtractive manufacturing, aerospace, automotive, consumer goods, industrial goods, orthodontics, orthopedics and related sectors and industries. In addition, three-dimensional scanners are commonly used in Augmented Reality ("AR") and Virtual Reality ("VR") devices. Each application requires certain features and qualities in a 3D model that is developed utilizing the scanners. For example, in orthopedics and orthodontics, speed, patient comfort, maintaining anatomical position, accuracy and precision are important parameters for the medical specialists. In AR and VR, the color data (red, green, blue ("RGB") point cloud) of the model is often more important than other factors.

In traditional methods for treating broken bones and injured joints, the patient's body part, such as the arm or foot, is immobilized by circulating roles of plaster, resin or fiberglass around the impacted body part or adjacent anatomy. Although the plaster, resin or fiberglass can be applied in a short time, there are shortcomings with prior art casting and related methods. Conventional casts are not resistant to water and lose their properties over time, which can have a negative impact on patient outcomes. The conventional plaster casts severely limit activity of the patient by requiring avoidance of water, limiting sweating and otherwise avoiding any activity that could introduce foreign substances into the space between the cast and the patient's skin. Another limitation of the traditional cast is the continuous and solid nature of the final casts that do not include a lattice or holes therein to allow air flow though the cast to avoid or limit sweating and subsequently avoid or limit skin itching, as well as to monitor and treat the patient's skin. The lack of lattice or holes also prevents foreign substances from being removed from the patient's skin when captured in internal spaced between the inner surface of the cast and the patient's skin, which can cause severe irritation by rubbing against the patient's skin. The patient's skin may require or benefit from treatment due to skin injuries or irritation resulting from a trauma that also causes the patient's injury or as a result of foreign object irritation while wearing the cast. In the conventional casting system and process, the patient is required to keep their body part, such as an arm or foot, immobile for a long time before the cast dries and hardens and the rigid cast may result in immobilization of a joint near or at the patient's injury location. It would be desirable to design, deploy and distribute a system for manufacturing a cast or orthopedic orthosis that may be completed in shorter amounts of time and requires no or minimal contact with the patient's impacted body part.

Laser scanners may be constructed or adapted for portability or may be constructed or adapted for hand-held use. The laser scanner may be coupled to a robotic arm or Articulated Arms Coordinate Measuring Machines ("AACMM") for automated processing. For these scanners, the operator or the robotic arm turns or moves the object around to capture all or most of the points on the surface of the object. In these rotating 3D scanners, the process of capturing all or most points of the body part, such as a hand or foot, takes between one to five minutes (1-5 min), which is a significant period of time for a typical patient to hold the body part, such as the arm, foot or other body part, in a generally immobile position without movement during the scanning process. There are other methods of 3D scanning such as photogrammetry in which ten to twenty (10-20) digital single-lens reflex ("DSLR") cameras are set at fixed positions around the object to capture two-dimensional ("2D") images and the 2D images are merged into a 3D point cloud or to facilitate development of a 3D model. Although this method is relatively quick during processing, it is not a cost-effective process for medical applications. The casts, splints, braces and other orthoses are also preferably manufactured in the most efficient and accurate manner after the 3D model of the patient's limb is prepared. Manufacturing the casts, splints, braces and other orthoses utilizing additive manufacturing based on a 3D model of the limb can be time consuming and expensive. This particular system and method also requires a designated space for the set-up, which may not be possible in all medical facilities. There is another type of photogrammetric 3D-scanning in which one camera is turned around the object to provide twenty to forty (20-40) photos of the object. This method is cost-effective but lacks speed, accuracy, precision and is mostly used for in-home applications. The preferred 3D scanner and related methods address the shortcomings of the prior art devices and methods to provide an accurate scan of a patient's anatomy, transform the scan into a 3D model, define a cast or splint based on the 3D model and is optimized for rapid manufacturing of the product that is used in patient care. The preferred 3D subtractive manufacturing process also addresses additional shortcomings of the prior art, as is described in greater detail below.

BRIEF SUMMARY OF THE INVENTION

Briefly stated, the preferred invention is directed to a 3D subtractive manufacturing system configured for constructing an orthopedic orthosis from a first blank of a plurality of blanks for a patient. The 3D subtractive manufacturing system includes a scanner configured to capture a 3D model of a body part of the patient, a central processor configured to receive the 3D model and select the first blank based on the 3D model and a computer numerical control machine configured to receive the computer numeric control programming file and an identification of the first blank from the central processor. The central processor configured to convert the 3D model into a computer numeric control programming file. The computer numerical control machine is comprised of a subtractive manufacturing machine. The computer numerical control machine is configured to remove material from the first blank to form the orthopedic orthosis.

In another aspect, the preferred invention is directed to a scanner system for capturing a 3D model of a body part of a patient. The scanner system includes a light source configured to project a stripe of light to illuminate the body part, a sensor configured to capture 2D and 3D images of the body part, a housing configured to support the light source, the sensor and a central processor configured to receive the two-dimensional and three-dimensional images of the body part from the sensor and convert the two-dimensional and three-dimensional images into a three-dimensional model of the body part. The housing includes an opening configured to receive the body part therein.

A scanner system for capturing a 3D model of an object including a light providing a stripe of light to illuminate the object, a capturing device to capture 2D and 3D images of the object, a holder configured to hold the capturing device, a central processor configured to receive data collected from the capturing devices, send commands and process data, a mechanical structure comprised of an open box to fix the capturing devices, and a graphical user interface to assist the patient limb positioning based on the clinical requirements with augmented reality ("AR") or virtual reality ("VR"), process the two-dimensional and three-dimensional images and construct a 3D model. The graphical user interface configured to navigate over a 3D model of the object. The capturing device may include a camera, a sensor, a tablet, or a smartphone. The mechanical structure configured to receive the object.

In another aspect, the preferred invention is directed to 3D subtractive manufacturing of casts, braces, splints and other orthoses that is relatively efficient and straight-forward for quick production of the cast, brace, splint or other orthoses at the point of patient care. The preferred system utilizes augmented reality scanning solutions to improve fit, comfort and accuracy for the clinician and patient. 3D subtractive methods for manufacturing orthoses, preferably orthopedic orthoses allows for rapid turnaround for creation of the product to be applied to the patient for prompt immobilization of the impacted area. The production method streamlines and optimizes the process to expedite patient care and is novel compared to prior art practices.

In a further aspect, the preferred invention is directed to a scanner system for capturing a 3D model of an object including a light providing a stripe of light to illuminate the object, a capturing device to capture 2D and 3D images of the object, a holder configured to hold the capturing device, a central processor configured to receive data collected from the capturing devices, send commands and process data, a mechanical structure comprised of an open box to fix the capturing devices, and a graphical user interface to process the two-dimensional and three-dimensional images and construct a 3D model. The graphical user interface configured to navigate over a 3D model of the object. The capturing device may include a camera, a sensor, a tablet, or a smartphone. The mechanical structure configured to receive the object.

In another aspect, the preferred invention is directed to 3D subtractive manufacturing of casts, braces, splints and other orthoses that is relatively efficient and straight-forward for quick production of the cast, brace, splint or other orthoses at the point of patient care. The preferred system utilizes mass-customization molds and customization machining for rapid turnaround to create the product to be applied to the patient for prompt immobilization of the impacted area.

BRIEF DESCRIPTION OF THE SEVERAL VIEWS OF THE DRAWINGS

The foregoing summary, as well as the following detailed description of preferred embodiments of the orthopedic orthosis, instrument, system, implant and method of the present application, will be better understood when read in conjunction with the appended drawings. For the purposes of illustrating the 3D subtractive manufacturing system and method for manufacturing orthopedic orthoses, including splints, braces, casts and other orthoses, there are shown in the drawings preferred embodiments. It should be understood, however, that the application is not limited to the precise arrangements and instrumentalities shown. In the drawings.

DETAILED DESCRIPTION OF THE INVENTION

Figure 1:
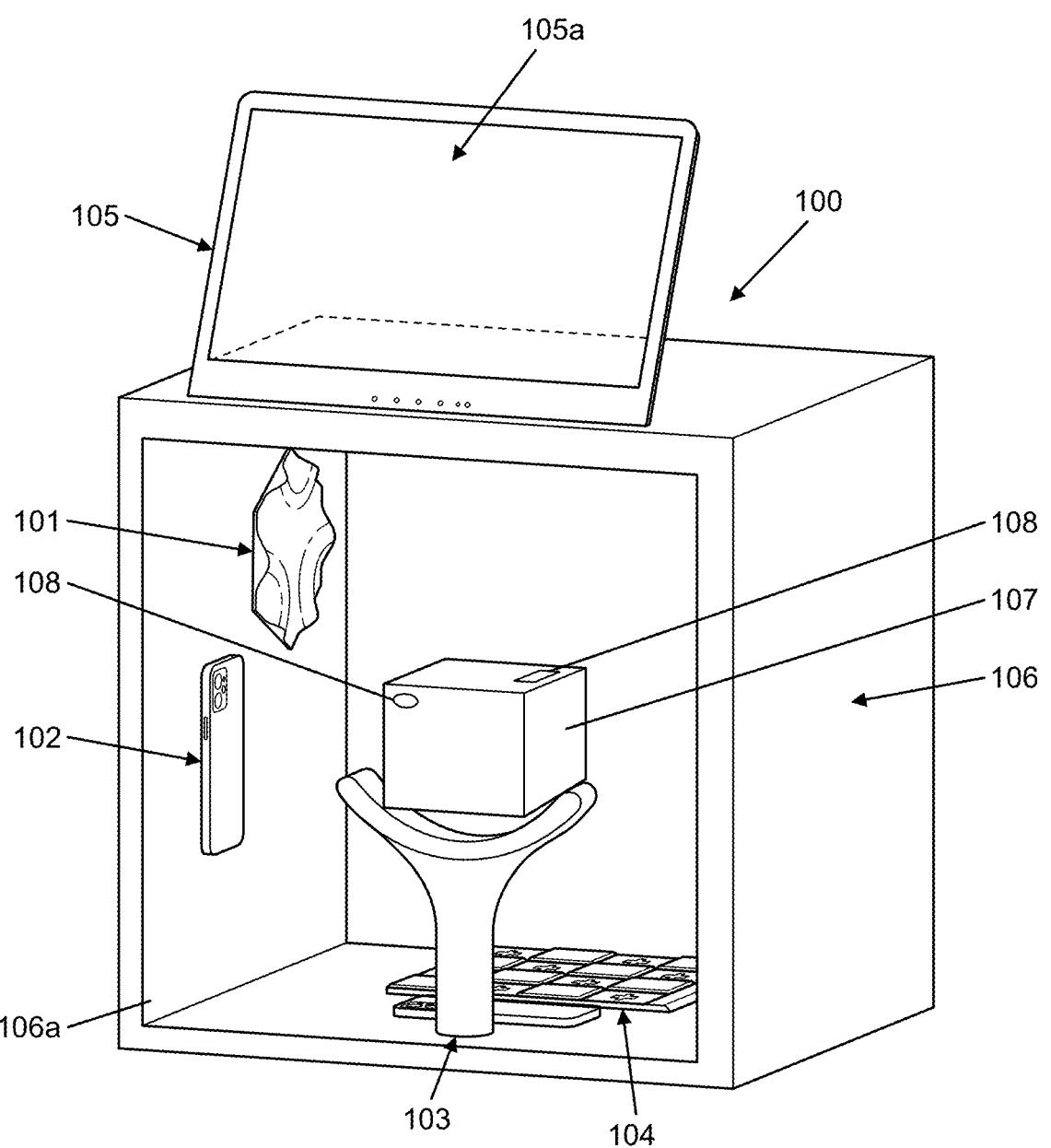
FIG. 1 illustrates a side perspective view of a 3D or stationary scanner, including a uniform light or light source, a limb holder, a housing or mechanical structure, a central processor and a sensor or camera in accordance with a preferred embodiment of the present invention.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred scanner system, 3D subtractive manufacturing system, orthopedic orthoses or casts, splints, braces or other orthoses and related parts thereof. The words, "anterior", "posterior", "superior," "inferior," "lateral," "ulnar," "radial" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIG. 1, components of a three-dimensional scanner 100 and associated central processor 105 include a uniform light source 101, a 3D and/or 2D camera or sensor 102, a limb holder 103 to rest the patient's body part 107, such as a hand or another anatomy, a checkerboard 104, camera recognition or calibration indicator 104 that assists gauging sizes and shapes of a scanned object, a monitor 105a, central processor or processing unit 105 and a mechanical structure or housing 106. The camera or sensor 102 may be comprised of TrueDepth or light detection and ranging ("LiDAR") cameras or sensors that are able to create depth or 3D models based on 2D image capture or utilizing several 2D and/or 3D images. The sensor 102 is not limited to being comprised of TrueDepth or LiDAR cameras or sensors and may be comprised of any sensor, camera or sensors that are able to collect and image or images of the body part 107 and communicate with the central processor 105 to facilitate performance of the functions of the preferred system described herein, including capturing the 3D model of the body part 107 or capturing images that facilitates creation of the 3D model of the body part 107 by the central processor 105.

In operation, the central processor 105 preferably calibrates the camera or sensors 102 with a calibration indicator 104, which is comprised of a checkerboard 104 in the preferred embodiment but is not so limited. The system is not limited to inclusion of the calibration indicator 104 and may be otherwise designed and configured for operation, such as by operating without calibration or by operating recognizing the body part 107 or another object. The system is not limited to scanning and modelling the body part 107 and may be operated with nearly any object that is able to fit into the housing 106 and can be imaged by the sensor 102. The system, however, is utilized to image the body part 107, such as the patient's arm, hand, wrist, leg, foot, ankle, knee, hip, torso, back, neck, finger or other body part or portion. The subject body part 107 is preferably positioned on the holder 103 to orient and generally maintain the position of the body part 107 during scanning. The central processor 105 preferably assists the patient in visualizing a desired positioning of the body part 107 in the housing 106 and on the holder 103, such as by augmented or virtual reality ("AR" or "VR"), as positioning of the body part 107 on the holder 103 and within the housing 106 relative to the sensor 102 may be desired for collection of the images with the sensor 102 and subsequent creation of the 3D model. Positioning of the body part 107 in a predetermined position based on the particular body part 107 and the injury is desirable for preferred visualization of the body part 107 for image collection and the AR and/or VR can assist the patient with positioning the body part 107 in the desired position and orientation. The mechanical structure or housing 106 of the 3D scanner 100 can be adjusted in size, including in length, width, height and depth or in nearly any shape that accommodates a particular body part, such as a barrel or cylindrical shape, to fit the body part 107 therein, such as the patient's hand, wrist, arm, torso, neck, leg, knee, ankle, fingers, toes, hip or other body part or object that is being scanned.

The 3D processing procedure for the 3D scanner 100 preferably involves taking red, green and blue ("RGB") images along with LiDAR and TrueDepth data utilizing the sensor 102. Advanced computerized tomography ("CT") scanning, magnetic resonance imaging ("MRI") and other medical image data can be integrated into the preferred process by adapting or utilizing multiple sensors 102. The data is preferably collected, calibrated, and processed with machine vision algorithms of the central processor 105 to form a 3D scanned file or a 3D model. The central processor 105 may utilize and algorithm, including machine vision and feature detection, in order to create the 3D scan or 3D model and fill any missing data points to find the best-matched object and deform a mesh with image processing algorithms as iterative closest Point ("ICP") to fill the missing part or parts of the scanned object, such as the body part 107.

Referring to FIGS. 1-9, in the preferred process, the 3D scanner 100 generates the digital scan file 201, 202 or the 3D model. The orthopedic orthosis, which may be comprised of a cast, splint, or brace designed for the specific body part 107, is preferably designed with customized automated 3D designing orthotics software 203. In the next preferred step, the software selects a pre-made mold or a blank from a plurality of blanks or molds from a blank or mold inventory

900 based on a minimum estimated production time 204. The central processor 105 determines the best fitted pre-made mold or blank 207 from the blank inventory 900. The blank inventory 900 preferably includes the pre-made molds or blanks for the orthopedic orthosis, such as casts, splints, and braces, including different sizes, colors, shapes, and materials 206. The selected blank may be optimized, and a computer numeric control programming file, such as a G-code file, may be generated based on the design and blank with the attached support 208. The desired orthopedic orthosis is manufactured by subtractive technology or computer numeric control ("CNC") machining techniques, such as milling, laser engraving, lathes, drilling, combinations and related techniques 209. If an appropriately sized and shaped pre-made mold or blank is unavailable, the process may be performed by additive manufacturing technology, simultaneously generating the pre-made mold or blank and the requested part 205. The final product or orthopedic orthosis may be post-processed with various post-processing methods or processes, including ultraviolet ("UV") processing, sandblasting, coating, buffing or any desired post-processing procedure 210. The finished product, preferably the final orthopedic orthosis, may be delivered to the clinic or any location to fit the manufactured orthopedic orthosis, such as a cast, splint, or brace 211, 212.

Figure 2:
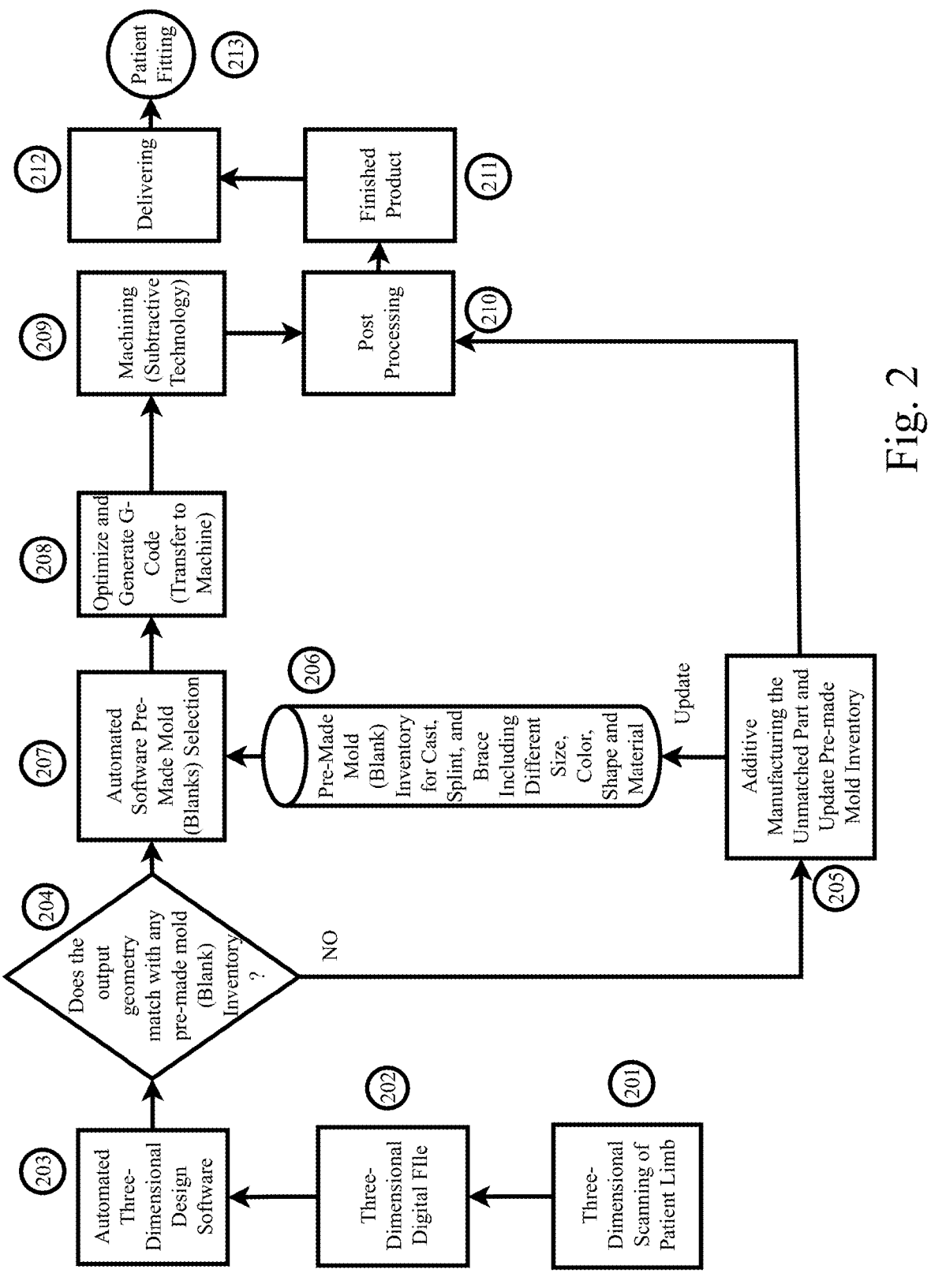
FIG. 2 is a block diagram flowchart of a method of manufacturing an orthopedic orthosis utilizing subtractive manufacturing technology in accordance with a preferred embodiment of the present invention.
Figure 3:
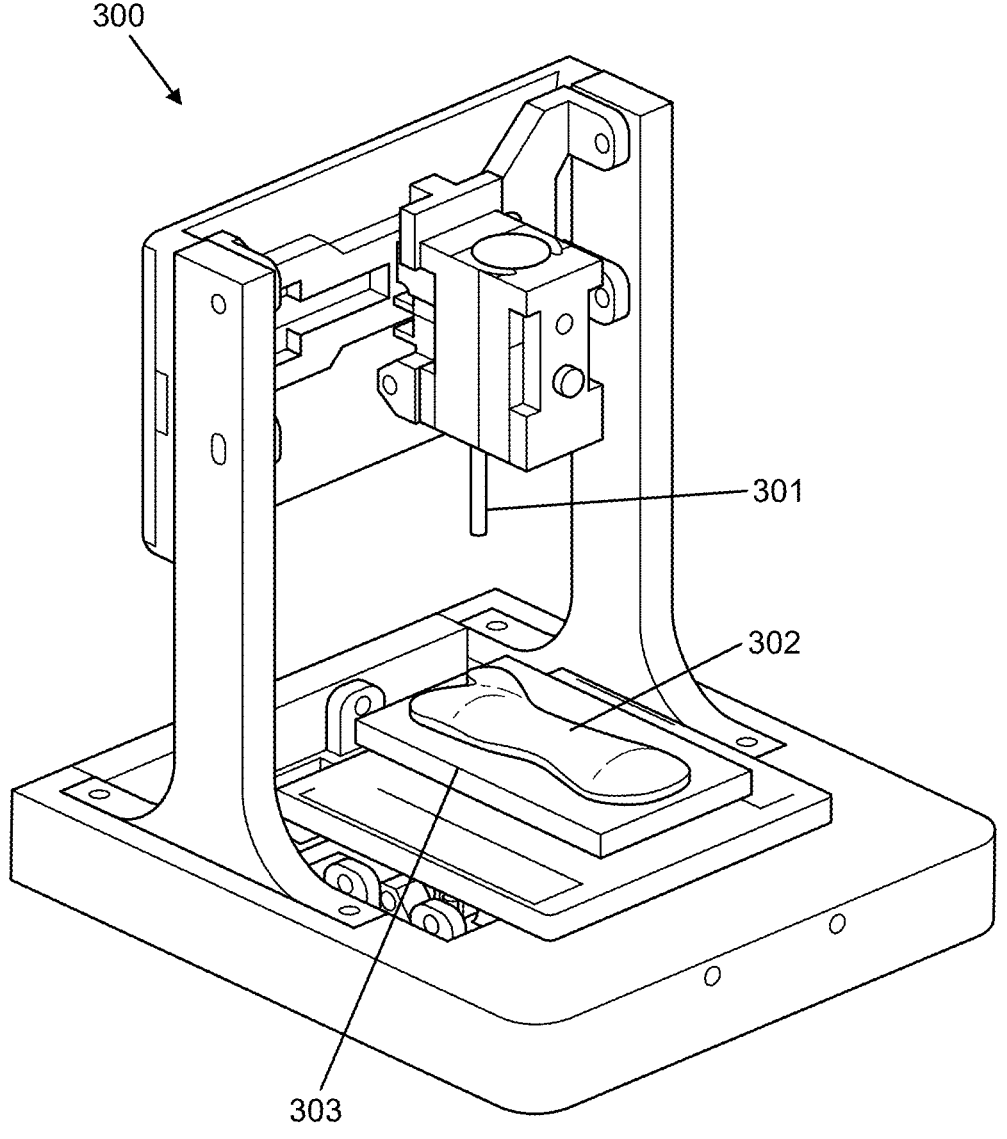
FIG. 3 is a side perspective view of a subtractive machining mechanism or computer numerical control machine for manipulating a blank, a block or a dorsal splint in accordance with a preferred embodiment of the present invention.

Referring to FIG. 3, a CNC machine 300 may be utilized to manufacture the orthopedic orthosis, such as a cast, splint or brace. The machining steps may generally be comprised of the CNC machine 300 receiving a selection of a first blank from the central processor 105 based on the 3D model 207, potentially using additive manufacturing techniques to add material for unmatched parts or voids where the 3D model indicates material should be included 205, receiving information from the central processor 105 related to the blank inventory 900, the case, splint or brace to be manufactured, the blank and final orthopedic orthosis size, color, shape and material 206, optimizing the computer numeric control programming file, such as G-code, for manufacture of the orthopedic orthosis 208 and machining the orthopedic orthosis 209, as represented in FIG. 2. The subtractive machining process is typically comprised of three major components, which include the CNC machine 300 with a bit or a laser engraver 301, the pre-made mold or blank 302 that is preferably loaded into the CNC machine 300 where the CNC machine 300 follows the subtraction contour to produce the output product or the orthopedic orthosis and a block part 303 in various shapes, colors, and thicknesses are preferably utilized to support the construct during machining. The blank 302 may be in the shape of a cylinder, the shape of a cone, or an outline of a block. The pre-made mold or blank 302 can be manufactured by a 3D-printing process when the block part 303 is unavailable in the inventory or is an alternative subtractive manufacturing process utilizing only the block part 303 or the blank 302 that is machined directly by the CNC machine 300.

Figure 4:
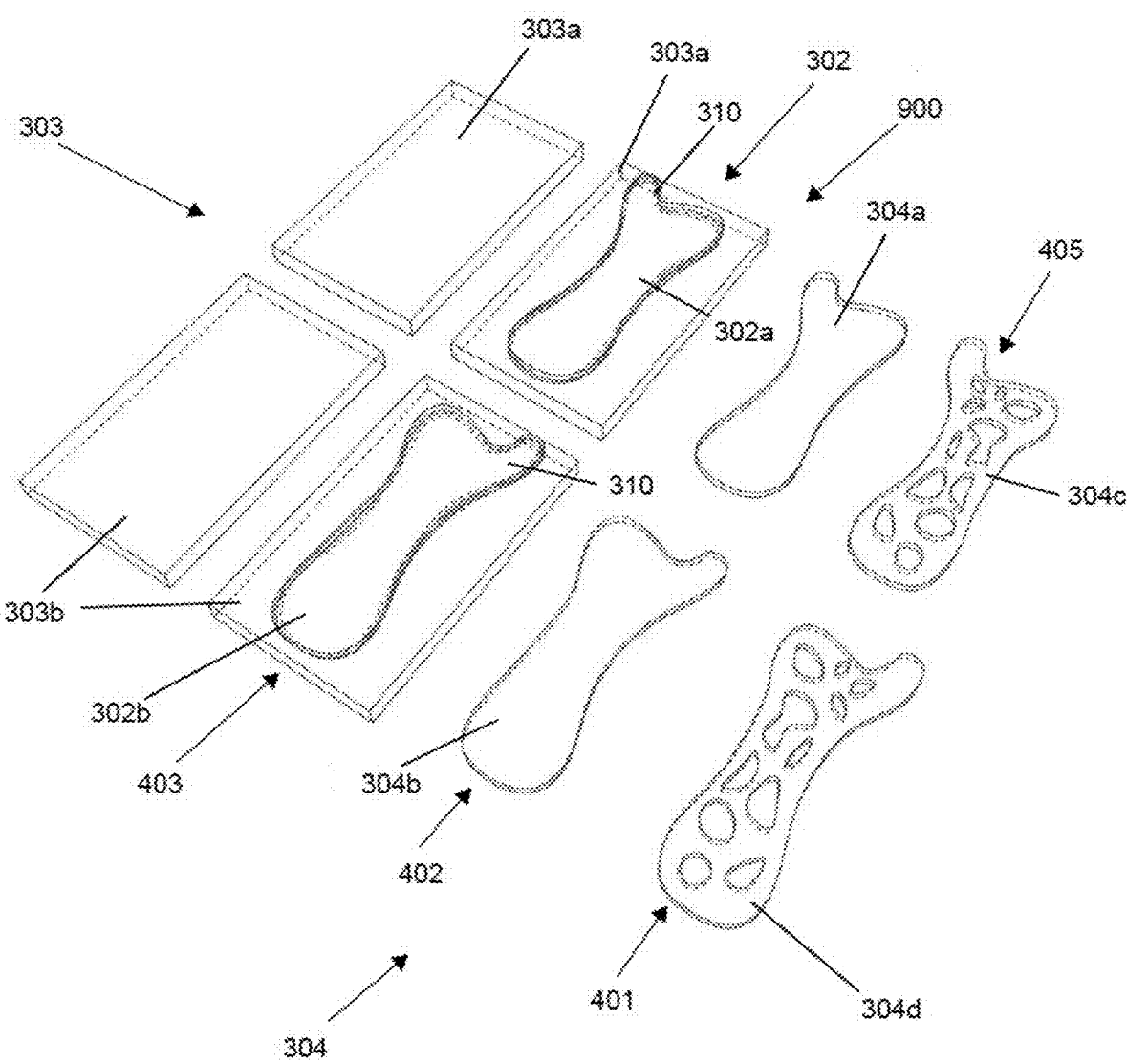
FIG. 4 is top perspective view of blanks, blocks and orthopedic orthoses that may be constructed utilizing the 3D scanner and method of FIGS. 1 and 2 and representing a machining process for transforming the blanks and blocks into the orthopedic orthosis or an arm, wrist and hand splint or cast, in accordance with a preferred embodiment of the present invention.
Figure 6:
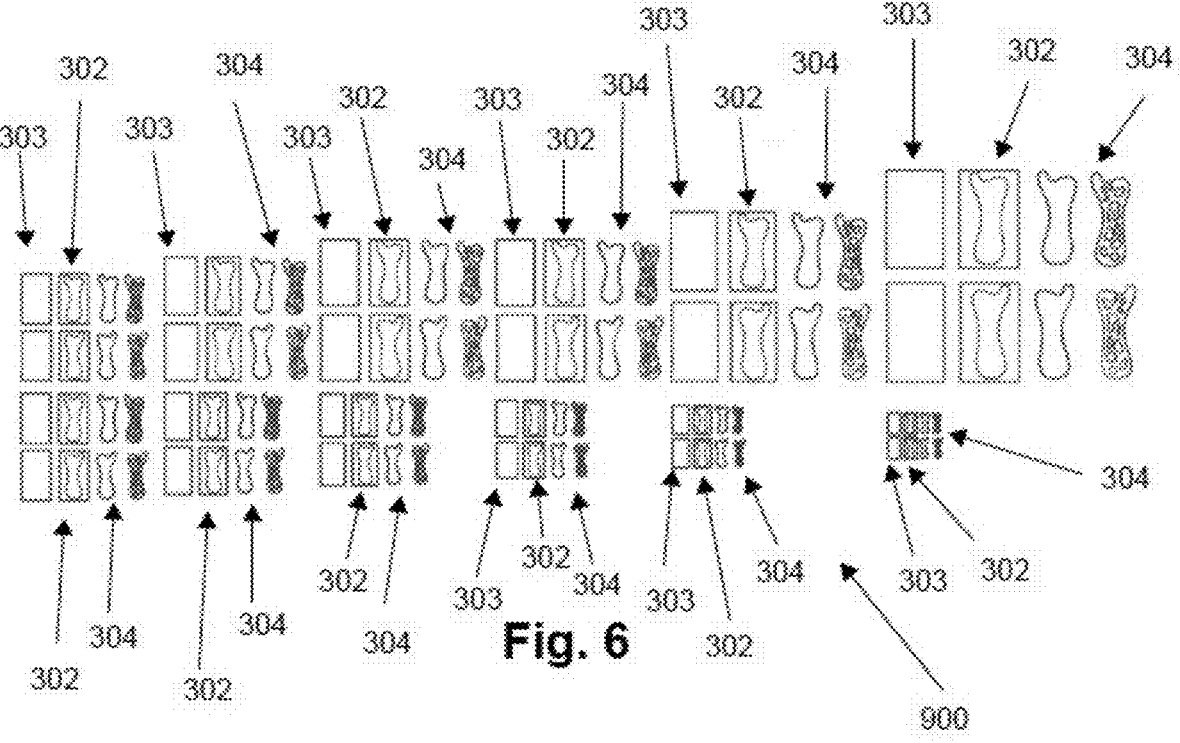
FIG. 6 illustrates top plan views of blocks, blanks and orthopedic orthoses in a mold or blank inventory, wherein the inventory includes various sizes, shapes, product types and stages of blocks, blanks and orthopedic orthoses in accordance with a preferred embodiment of the present invention.

Referring to FIGS. 4 and 6, an illustrative subtractive manufacturing process for a splint or cast is shown in four steps. The pre-made mold or blank 302 is selected based on the required shape, size, color, and porosity of the desired final orthopedic orthosis by the central processor 105 based on the 3D model in an initial step 207, which may be comprised of a generally box-shaped blank 303. The box-shaped blank 303 is preferably retrieved from the mold or blank inventory 900 with multiple sizes for the desired splint in an initial step 404. The contour is preferably milled and machined based on the CNC programming file, such as G-code, with the CNC machine 300 in another step 403. The lattice and support are preferably also generated with machining using the CNC machine 300 in a further step 401 or the blank 302 may initially include pre-defined lattice therein. The final product or orthopedic orthosis is ready to be delivered and fitted to the patient after a post-processing step 405 that may include coating, other surface treatments, inclusion of additional padding or comfort materials, attachment of movable portions to accommodate movement of the patient's body part, such as at the wrist, elbow, knee or ankle, application of medicament to surfaces or other post-processing steps.

Figures 5A, 5B:
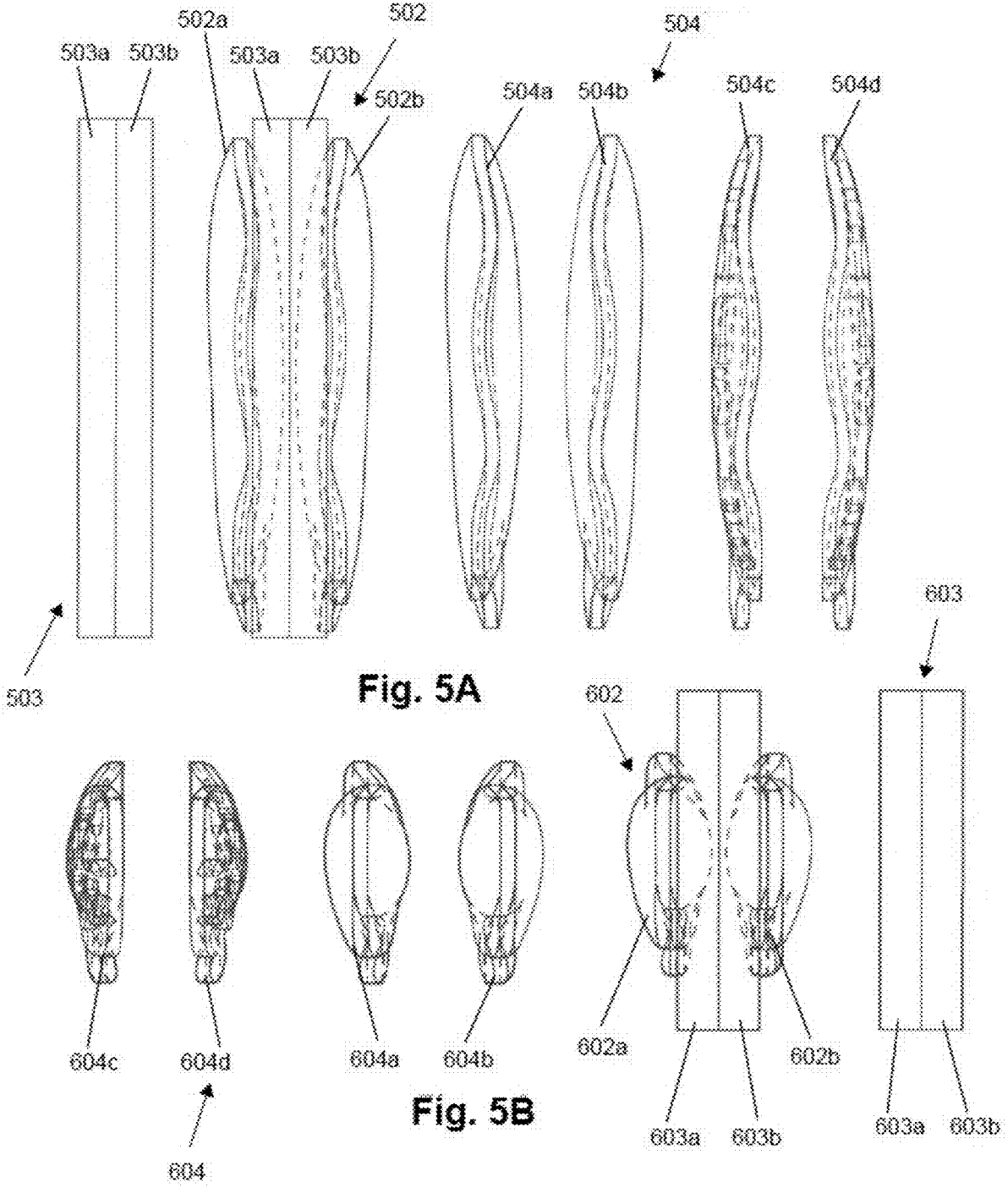
FIG. 5A illustrates side elevational views of blanks, blocks and orthopedic orthoses that may be constructed utilizing the 3D scanner and method of FIGS. 1 and 2, wherein the orthopedic orthosis may be a volar wrist splint or cast or a forearm splint or cast in accordance with a preferred embodiment of the present invention.
FIG. 5B illustrates side elevational views of blanks, blocks and orthopedic orthoses that may be constructed utilizing the 3D scanner and method of FIGS. 1 and 2, wherein the orthopedic orthosis may be a hand or wrist splint or cast in accordance with a preferred embodiment of the present invention.

Referring to FIG. 4, in the preferred embodiment, the process includes utilizing two blocks 303, including first and second blocks 303a, 303b and two blanks 302, including first and second blanks 302a, 302b. The 3D cast or orthopedic orthosis 304 may be made in two or more portions from different shaped blanks 302 in a similar process. Referring to FIGS. 5A and 5B the preferred process may also be utilized to construct second and third preferred orthopedic orthoses 504, 604. The second and third preferred embodiments also include the blanks 502, 602, including the first and second blanks 502a, 502b, 602a, 602b, the blocks 503, 603, including the first and second blocks 503a, 503b, 603a, 603b and the orthotic orthoses 504, 604, including the first and second solid and latticed orthoses 504a, 504b, 504c, 504d, 604a, 604b, 604c, 604d. The second and third preferred blanks 502, 602 and blocks 503, 603 are preferably included in the mold or blank inventory 900 for selection by the central processor 105 and machining utilizing the CNC machine 300.

Figures 7A, 7B, 7C, 7D, 7E:
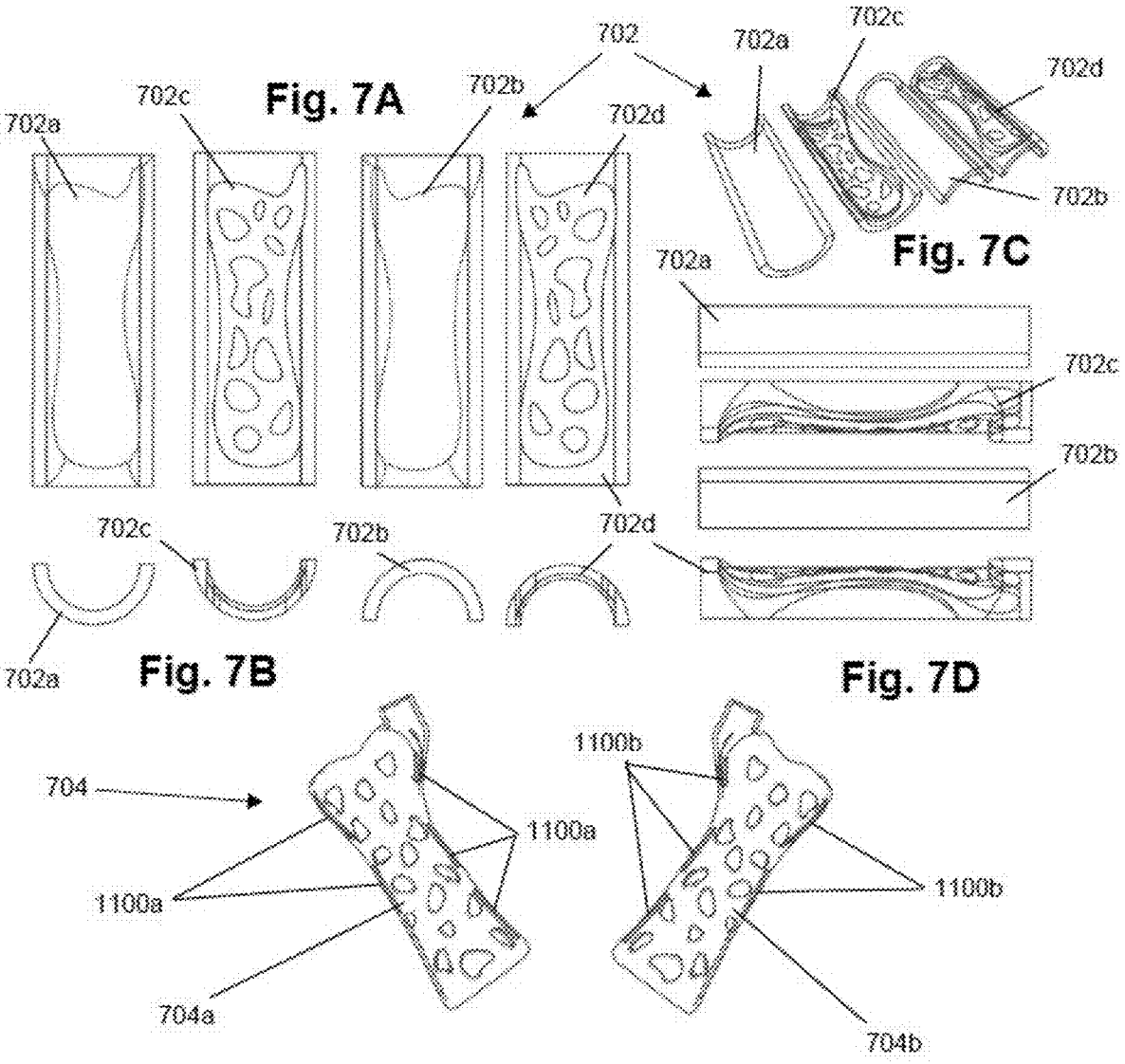
FIG. 7A illustrates various top plan views of blanks of the mold or blank inventory of FIG. 6, particularly blanks of a plurality of blanks for an arm, hand and/or wrist splint or cast in accordance with the preferred embodiment of FIG. 6.
FIG. 7B illustrates rear elevational views of the blanks of FIG. 7A.
FIG. 7C illustrates bottom perspective views of the blanks of FIG. 7A.
FIG. 7D illustrates side elevational views of the blanks of FIG. 7A.
FIG. 7E illustrates top perspective views of first and second portions of an orthopedic orthosis constructed from one of the plurality of blanks of FIG. 7A, particularly an arm, hand and wrist splint or cast.

Referring to FIG. 7, in a fourth preferred embodiment, an alternative plurality of blanks 702, including first and second solid blanks 702a, 702b and first and second latticed blanks 702c, 702d may be utilized by the system to construct a fourth preferred orthopedic orthosis 704. The fourth preferred blanks 702 has the general shape of a cylinder when combined into pairs and are relatively close to the final shape of the orthopedic orthosis 704, including the first and second latticed orthoses 704a, 704b, of the fourth preferred embodiment that is constructed from machining and securing together the semi-cylindrical first and second latticed blanks 702c, 702d or by also machining lattice into the first and second solid blanks 702a, 702b. The CNC machine 300 preferably cuts the contour based on the CNC programming file, preferably the G-code, from the central processor 105 to produce the final cast or orthopedic orthosis 704, including the first and second latticed orthoses 704a, 704b. the CNC machine 300 may, accordingly, form the first and second latticed orthoses 704a, 704b by machining the first and second solid blanks 702a, 702b or the first and second latticed orthoses 702c, 702d to define the final cast or splint, which is preferably comprised of the arm, wrist and hand orthosis 704 of the fourth preferred embodiment.

Figures 8A, 8B, 8C, 8D, 8E:
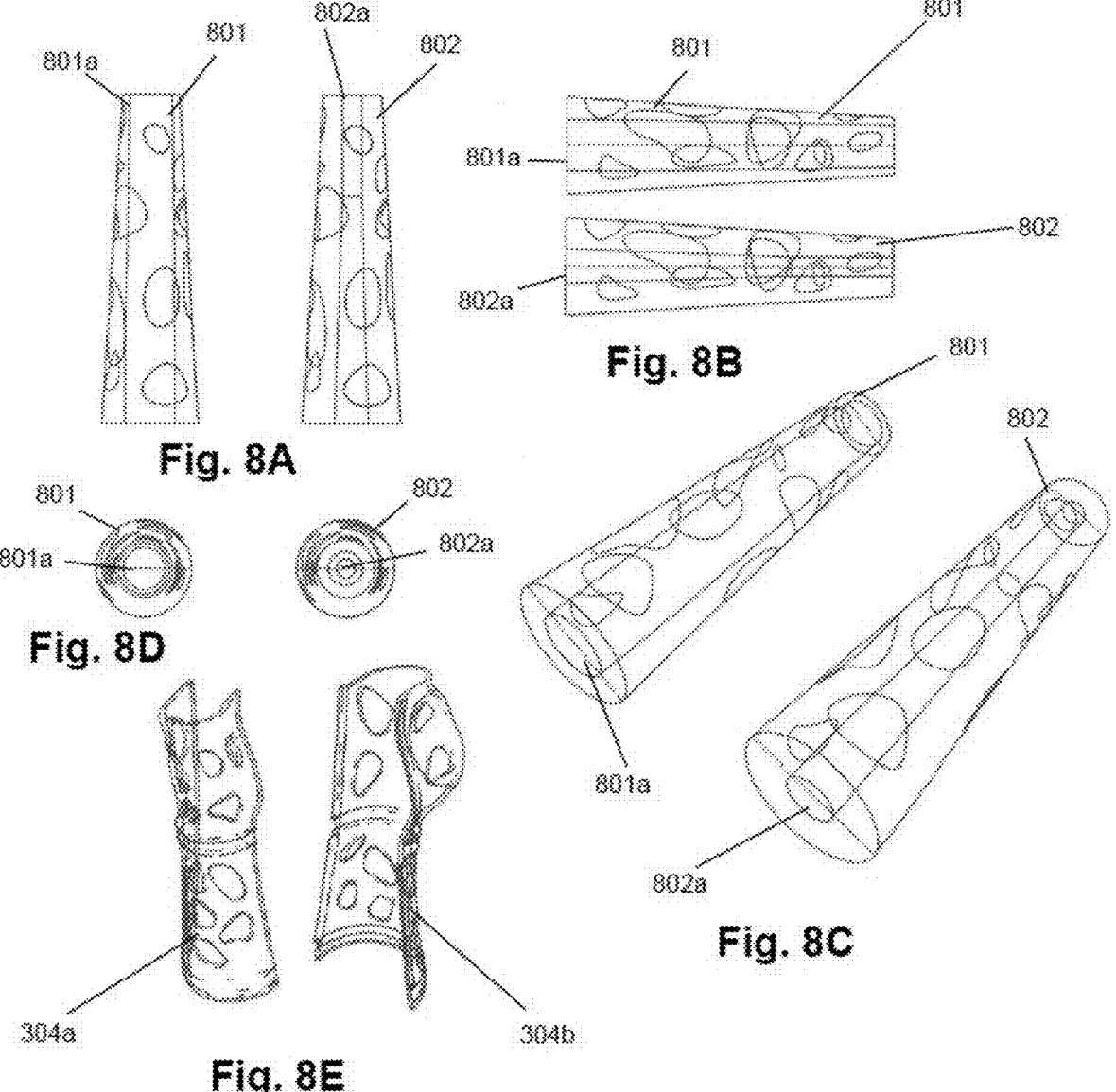
FIG. 8A illustrates top plan views of blanks of a mold or blank inventory in accordance with a preferred embodiment of the present invention, particularly blanks for an arm, hand and wrist splint.
FIG. 8B illustrates side elevational views of the blanks of FIG. 8A.
FIG. 8C illustrates top perspective views of the blanks of FIG. 8A.
FIG. 8D illustrates rear elevational views of the blanks of FIG. 8A.
FIG. 8E illustrates a side elevational view of first and second portions of an orthopedic orthosis constructed from one of the blanks of FIG. 8A, particularly an arm, wrist and hand splint or cast.

Referring to FIG. 8, in a fifth preferred embodiment, the system may utilize first and second latticed blanks 801, 802 having a truncated hollow cone shape that are substantially identical but may a larger hollow 801a in the first latticed blank 801 compared to a smaller hollow 802a in the second latticed blank 802 or may be pre-serrated for separation. The first and second latticed blanks 801, 802 are preferably separated by the CNC machine 300 to construct the orthopedic orthosis 804, including first and second latticed orthoses 804a, 804b.

Figures 9A, 9B, 9C:
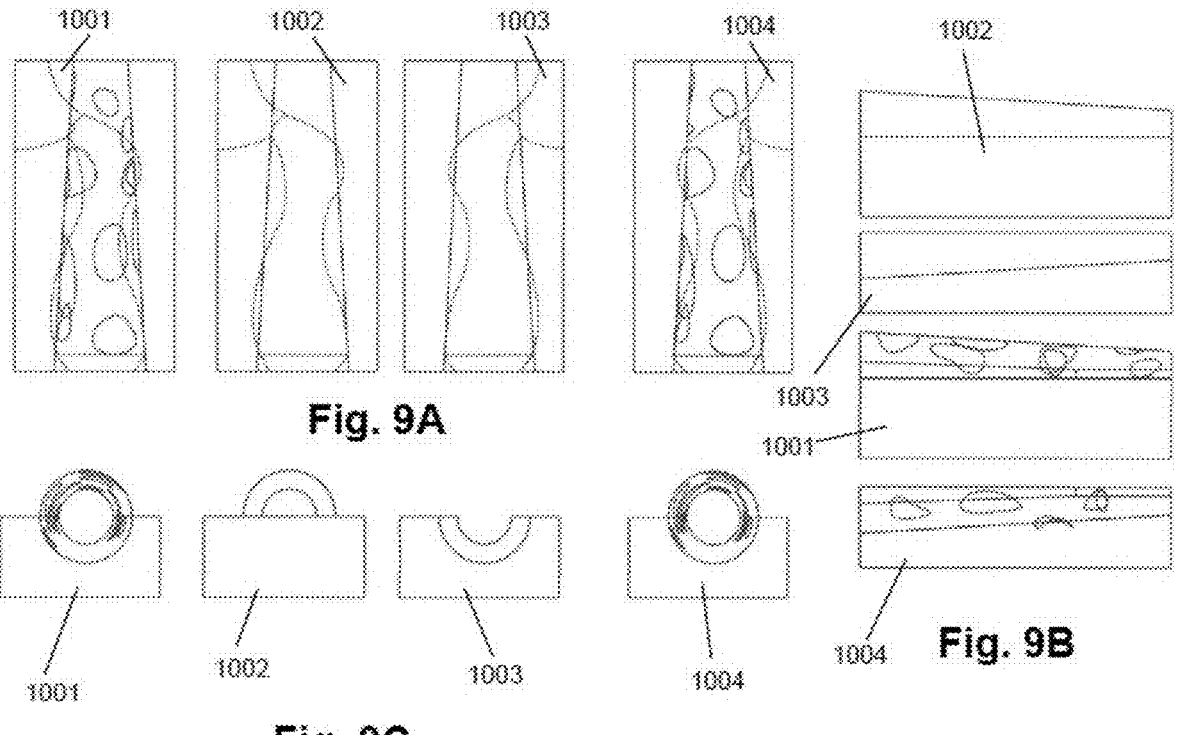
FIG. 9A illustrates top plan views of blanks of a mold or blank inventory in accordance with a preferred embodiment of the present invention, particularly blanks for arm and wrist splints.
FIG. 9B illustrates side elevational views of the blanks of FIG. 9A.
FIG. 9C illustrates rear elevational views of the blanks of FIG. 9A.

Referring to FIG. 9, in a sixth preferred embodiment, the system may utilize first, second, third and fourth blocks 1001, 1002, 1003, 1004 having various partial truncated hollow cone shapes and latticed features that may be machines by the CNC machine 300 to define the final orthopedic orthosis constructed of a unitary cast or brace or having first and second portions that are connected to define the final orthopedic orthosis. are the illustrations for the 3D cast of the cylinder and the block.

Referring to FIGS. 1-9, the preferred invention is directed to a 3D subtractive manufacturing system configured for constructing the orthopedic orthoses 304, 504, 604, 704, 804 from a first blank 302, 502, 602, 702, 801, 802 of a plurality of blanks or a block or blank inventory 900. The 3*d* subtractive manufacturing system includes the scanner 100, the central processor 105 and the CNC machine 300. The scanner 100 is configured to capture the 3D model of the body part 107 of the patient and the central processor 105 is configured to receive the 3D model and select the first blank 302, 502, 602, 702, 801, 802 based on the 3D model. The central processor 105 converts the 3D model into a CNC programming file, such as a G-Code file, that may be transmitted to the CNC machine 300 to construct the orthopedic orthosis 304, 504, 604, 704, 804 from the first blank 302, 502, 602, 702, 801, 802. The first blank 302, 502, 602, 702, 801, 802 is preferably selected from the blank inventor 900 based on the 3D model that is received and/or developed by the central processor 105.

The preferred system includes a post processing unit, which may be comprised of the CNC machine 300, to remove a support from the orthopedic orthosis 304, 504, 604, 704, 804 and to surface treat the orthopedic orthosis 304, 504, 604, 704, 804. The CNC machine 300 may be adapted to remove the support from the orthopedic orthosis 304, 504, 604, 704, 804 by utilizing different tools and may also be utilized to surface treat or finalize the orthopedic orthosis 304, 504, 604, 704, 804 for appearance and/or comfort purposes.

The system may be configured to construct orthopedic orthoses 304, 504, 604, 704, 804 for various patient body parts. The body parts may include an arm, a wrist, a leg, a hand, a knee and an ankle. The plurality of blanks or blank inventory 900 may include arm blanks, wrist blanks, leg blanks, hand blanks, knee blanks, ankle blanks and additional blanks 302, 502, 602, 702, 801, 802, as well as various blocks 303, 503, 603, 1001, 1002, 1003, 1004 that are configured to be subtractively manufactured to define orthopedic orthoses that are adapted for the various subject body parts.

The central processor 105 is configured to track used blanks 302, 502, 602, 702, 801, 802, as well as the blocks 303, 503, 603, 1001, 1002, 1003, 1004 of the plurality of blanks or blank inventory 900 based on the identification of the first blank **302*a*, 502*a*, 602*a*, 702*a*, 801 as well as the blocks 303, 503, 603, 1001, 1002, 1003, 1004 that are used during the manufacturing processes. The central processor 105 may predict needs for replenishment of the first blank 302*a*, 502*a*, 602*a*, 702*a*, 801 as well as the blocks 303, 503, 603, 1001, 1002, 1003, 1004 so that the blank inventory 900 may be replenished. The central processor 105 may analyze patterns of the used first blank 302*a*, 502*a*, 602*a*, 702*a*, 801, as well as the blocks 303, 503, 603, 1001, 1002, 1003, 1004** for inventory optimization.

The central processor 105 may include an automatic modeling software that creates the 3D model to select the first blank **302*a*, 502*a*, 602*a*, 702*a*, 801 or the blocks 303, 503, 603, 1001, 1002, 1003, 1004. The automatic modeling software is preferably configured such that if the plurality of blanks or blank inventory 900 does not include the first blank 302*a*, 502*a*, 602*a*, 702*a*, 801 or the blocks 303, 503, 603, 1001, 1002, 1003, 1004 or an irregular shape of the body part is detected, the central processor 105** suggests an additive manufacturing process.

The plurality of blanks or blank inventory 900 includes multiple sized blanks 302, 502, 602, 702, 801, 802 and blocks 303, 503, 603, 1001, 1002, 1003, 1004 that have overlap for the body part. The orthopedic orthosis 304, 504, 604, 704, 804 may be constructed from the first blank **302*a*, 502*a*, 602*a*, 702*a*, 801 and the second blank 302*b*, 502*b*, 602*b*, 702*b*, 802, as well as potentially the first and second blocks 303*a*, 303*b*, 503*a*, 503*b*, 603*a*, 603*b*, 1001, 1002, 1003 1004, that are machined for combination to define the orthopedic orthosis 304, 504, 604, 704, 804**.

The first and second blanks **302*a*, 502*a*, 602*a*, 702*a*, 801, 302*b*, 502*b*, 602*b*, 702*b*, 802 may be connected to each other with a latching mechanism 1100*a*, 1100*b* that is machined or formed into the first and second blanks 302*a*, 502*a*, 602*a*, 702*a*, 801, 302*b*, 502*b*, 602*b*, 702*b*, 802 or the first and second orthoses 304*a*, 304*b*, 304*c*, 304*d*, 504*a*, 504*b*, 504*c*, 504*d*, 604*a*, 604*b*, 604*c*, 604*d*, 704*a*, 704*b*, 804*a*, 804*b*. The latching mechanism 1100*a*, 1100*b* may be comprised of a snap-lock mechanism formed in the first and second blanks 302*a*, 502*a*, 602*a*, 702*a*, 801, 302*b*, 502*b*, 602*b*, 702*b*, 802 or the first and second orthoses 304*a*, 304*b*, 304*c*, 304*d*, 504*a*, 504*b*, 504*c*, 504*d*, 604*a*, 604*b*, 604*c*, 604*d*, 704*a*, 704*b*, 804*a*, 804*b* but is not so limited and may be comprised of alternative latching mechanisms that are able to connect to each other and how together to secure the first and second orthoses 304*a*, 304*b*, 304*c*, 304*d*, 504*a*, 504*b*, 504*c*, 504*d*, 604*a*, 604*b*, 604*c*, 604*d*, 704*a*, 704*b*, 804*a*, 804*b* to the body part 107. In the preferred embodiment, the latching mechanism 1100*a*, 1100*b* is comprised of first and second latching mechanisms 1100*a*, 1100*b* that snap lock together to secure the first and second orthoses 304*a*, 304*b*, 304*c*, 304*d*, 504*a*, 504*b*, 504*c*, 504*d*, 604*a*, 604*b*, 604*c*, 604*d*, 704*a*, 704*b*, 804*a*, 804*b*** together in a mounted configuration.

The preferred blanks 302, 502, 602, 702, 801, 802 and blocks 303, 503, 603, 1001, 1002, 1003, 1004 may have a pre-bent shape conforming generally to the body part 107 for which the blanks 302, 502, 602, 702, 801, 802 or blocks 303, 503, 603, 1001, 1002, 1003, 1004 are selected. The pre-bent shape is generally configured to limit the amount of subtractive manufacturing required to finally form the orthopedic orthoses 304, 504, 604, 704, 804 and for best fit to the body part 107.

Referring to FIGS. 4 and 6, the first and second blanks **302*a*, 302*b* may include a ninety degree portion 310 that is pre-formed in the first and second blanks 302*a*, 302*b* or may be machined into the first and second block parts 303*a*, 303*b* by the CNC machine 300. The ninety degree portion 310 is configured to accommodate an ulnar gutter where a hand meets a patient's fingers. The blanks 302, 502, 602, 702, 801, 802 and blocks 303, 503, 603, 1001, 1002, 1003, 1004 are not limited to inclusion of the ninety degree portion 310 and may include other or additional anatomic features or bends to accommodate joints associated with the patient's body part 107**, such as the knee, elbow, wrist, ankle or other joint.

Referring to FIGS. 1-9, the first blank **302*a*, 502*a*, 602*a*, 702*a*, 801 as well as the blocks 303, 503, 603, 1001, 1002, 1003, 1004 and additional blanks 302, 502, 602, 702, 802 may have a multicolor or patterned appearance, include logos or other indicators that are formed in these components during the subtractive manufacturing process. The blanks 302, 502, 602, 702, 802 and blocks 303, 503, 603, 1001, 1002, 1003, 1004 may have various colors, sizes and shapes for inclusion in the 900 blank or block inventory 900 for selection by the central processor 105 and machining with the CNC machine 300. The first blank 302***a*, 502*a*, 602*a*, 702*a*, 801 as well as the blocks 303, 503, 603, 1001, 1002, 1003, 1004 and additional blanks 302, 502, 602, 702, 802 may include holes and patterns prefabricated thereon that may be configured and designed for the specific final orthopedic orthoses 304, 504, 604, 704, 804.

The CNC machine 300 is configured to receive the CNC programming file and an identification of the first blank 302*a*, 502*a*, 602*a*, 702*a*, 801 from the central processor 105 during use, after the scanner 100 collects the images for creation of the 3D model of the body part 107. The CNC machine 300 is comprised of a subtractive manufacturing machine that is configured to remove material from the first blank 302*a*, 502*a*, 602*a*, 702*a*, 801 or any of the blanks 302, 502, 602, 702, 802 and blocks 303, 503, 603, 1001, 1002, 1003, 1004 to form the orthopedic orthosis 304, 504, 604, 704, 804.

The central processor 105 may include an inventory management processing unit that is configured to optimize the CNC programming file and production time of the orthopedic orthosis 304, 504, 604, 704, 804 by selection of the first blank 302*a*, 502*a*, 602*a*, 702*a*, 801 or any of the blanks 302, 502, 602, 702, 802 and blocks 303, 503, 603, 1001, 1002, 1003, 1004 and machining parameters implementation in the CNC programming file. The inventory management processing unit may optimize the programming language and production time by high precision pre-mold size selection and machining parameters implementation in the CNC programming file, which may be comprised of G-code.

Each of the plurality of blanks 302, 502, 602, 702, 802 and blocks 303, 503, 603, 1001, 1002, 1003, 1004 may be constructed by injection molding or additive manufacturing of a polymeric material but is not so limited and may be constructed of nearly any material formed by nearly any method that is able to produce the blanks 302, 502, 602, 702, 802 and blocks 303, 503, 603, 1001, 1002, 1003, 1004 having the desired sizes and shapes, withstand the normal operating conditions of the blanks 302, 502, 602, 702, 802 and blocks 303, 503, 603, 1001, 1002, 1003, 1004 and perform the preferred functions of the blanks 302, 502, 602, 702, 802 and blocks 303, 503, 603, 1001, 1002, 1003, 1004 described herein. The CNC machine 300 is preferably configured for subtractive manufacturing of the blanks 302, 502, 602, 702, 802 and blocks 303, 503, 603, 1001, 1002, 1003, 1004 to define the orthopedic orthosis 304, 504, 604, 704, 804.

The preferred invention is also directed to scanner system for capturing the images to define the 3D model of the body part 107 of the patient. The scanner system includes a light source 101 configured to project a stripe of light to illuminate the body part 107, a sensor 102 configured to capture the 2D and 3D images of the body part 107, a housing 106 configured to support the light source 101 and the sensor 102 and the central processor 105. The housing 106 includes an opening 106*a* configured to receive the body part 107 therein. The body part 107 is preferably introduced into the housing 106 through the opening 106*a* and onto the holder 103 to position the body part 107 in preparation for scanning or imaging with the sensor 102. The central processor 105 is configured to receive the 2D and 3D images of the body part 107 from the sensor 102 and convert the 2D and 3D images into a three-dimensional model of the body part 107.

In the preferred embodiment, a graphical user interface is utilized to process the 2D and 3D images. The graphical user interface is preferably configured to navigate over the 3D model. The graphical user interface may be displayed on the monitor 105*a* but is not so limited and the graphical user interface may be displayed on a separate device, such as a user's smartphone through an application, or at a remote processor or separate processor with a monitor or display of the scanner system. The graphical user interface and the central processor 105 may assist in directing the patient with augmented or virtual reality to position the body part 107 in the opening 106*a* of the housing 106 relative to the sensor 102 and the light source 101. The augmented or virtual reality may adjust a guide based on clinical need or preferred position of the body part 107 based on a known injury or a known orthosis pattern. The central processor 105 may also use artificial intelligence and computer vision based on a limb 3D database to reconstruct missing datapoints of the 3D model. The central processor 105 may further calibrate, contouring and reconstruct a scanned digital file of the 3D model based on the pre-marked calibration data on the body part 107 or other object. The central processor 105 may also configure contouring and reconstruct a scanned digital file of the 3D model based on the markers 108 or the pre-marked calibration data on the body part 107 and camera/sensor properties of the sensor 102.

The sensor 102 may be comprised of a camera that is mounted in a stationary position on the housing 106 but is not so limited. The sensor 102 may alternatively be comprised of a capturing devices, such as a TrueDepth camera, Lidar cameras or sensors, depth cameras or other cameras or sensors that are able to collect images or scans that may be used to define the 3D model of the body part 107. The sensor 102 or camera may be movably mounted to the housing 106 and configured to scan greater than fifty percent (50%) of the outer surface of the body part 107. The sensor 102 and capturing devices may include a camera, a sensor, a tablet, a smartphone, another scanning device or combinations of these devices that operate to scan the body part 107 and define the 3D model. The sensor 102 may be calibrated with the checkerboard or calibration indicator 104 to facilitate sizing and calibration of the sensor 102 during use. The checkerboard or calibration indicator 104 is preferably position on a floor of the housing 106 within the housing 106.

The preferred system may include markers 108 are positioned on the body part 107. The sensor 102 preferably captures images of the markers 108 and the central processor 105 is configured to utilize the markers 108 in the 2D and 3D images to calibrate the 3D model.

The central processor 105 may use an iterative, closest point or 3D reconstruction algorithm to reconstruct blind spots of the 3D model. An automated uniform-making process of the central processor 105 is configured to reconstruct incomplete surfaces of the body part 107 in the 3D model as the sensor 102 captures the 2D and 3D images.

The central processor 105 is preferably configured to define the CNC programming file such that the CNC machine 300 mills equal or more planes from the blanks 302, 502, 602, 702, 802 and/or blocks 303, 503, 603, 1001, 1002, 1003, 1004 to subtract material and form the orthopedic orthosis 304, 504, 604, 704, 804, which is preferably comprised of a cast, splint, brace or other orthoses. The blank inventory 900 may be derived from mass-customizing human limbs into multiple sizes, wherein each size of the plurality of blanks 302, 502, 602, 702, 802 and/or blocks 303, 503, 603, 1001, 1002, 1003, 1004 has overlap with another size or may be entirely independent. During use, the central processor 105 may calculate and predict a size, shape and color of the blanks 302, 502, 602, 702, 802 and/or blocks 303, 503, 603, 1001, 1002, 1003, 1004 based on input of the 3D model (scanned object), which is preferably defined by the central processor 105 based on the scans from the sensor 102. The blanks 302, 502, 602, 702, 802 and/or blocks 303, 503, 603, 1001, 1002, 1003, 1004 may have a multicolor or patterned appearance (3D or 2D pattern) for aesthetics or patient preferences.

Multiple blanks 302, 502, 602, 702, 802 and/or blocks 303, 503, 603, 1001, 1002, 1003, 1004 may be utilized to define the orthopedic orthosis 304, 504, 604, 704, 804, which is preferably comprised of a cast, splint, brace or other orthoses, based on the input CNC programming file, which is preferably comprised of G-code or a digital file of the patient's limb or body part 107. The orthopedic orthosis 304, 504, 604, 704, 804 may include the latching mechanism 1100a, 1100b that tightens or enlarges the orthopedic orthosis 304, 504, 604, 704, 804, which may be comprised of the cast, splint, brace or other orthoses. The latching mechanism 1100a, 1100b may be machined into or otherwise connected to the first and second blanks 302a, 302b 502a, 502b, 602a, 602b, 702a, 702b, 702c, 702d, 801, 802 or any of the blanks 302, 502, 602, 702, 802 and blocks 303, 503, 603, 1001, 1002, 1003, 1004. The latching mechanism 1100a, 1100b may be comprised of a strap or loop closure to immobilize the body part 107, preferably the patient's limb, in the orthopedic orthosis 304, 504, 604, 704, 804, which is preferably comprised of the cast, splint, brace or other orthoses.

The CNC machine 300 for construction of the orthopedic orthoses 304, 504, 604, 704, 804, which are preferably comprised of a cast, splint, brace or other orthoses, may be comprised of laser cutters, milling machines, drills or other CNC machines for machining the blanks 302, 502, 602, 702, 802 and/or blocks 303, 503, 603, 1001, 1002, 1003, 1004 into the orthopedic orthoses 304, 504, 604, 704, 804.

The central processor 105 may be configured to utilize 3D mapping and contouring to determine geometrical data of cut place and shape/pattern per a patient's 3D scan or digital input when defining the CNC programming file for subtractive machining of the blanks 302, 502, 602, 702, 802 and/or blocks 303, 503, 603, 1001, 1002, 1003, 1004 during use. The central processor 105 may also develop the CNC programming file to include multiple portions of the blanks 302, 502, 602, 702, 802 and/or blocks 303, 503, 603, 1001, 1002, 1003, 1004 and the multiple portions can be pared and manipulated to make the orthopedic orthoses 304, 504, 604, 704, 804 that may be assembled into the preferred cast, splint, brace or other orthopedic orthoses.

The system may include a positioning jig (can be produced with subtractive or additive manufacturing) for placing the orthopedic orthoses 304, 504, 604, 704, 804, preferably the cast, splint, brace or other orthoses, onto the patient's body part 107. The positioning jig may be positioned back into the CNC machines 300 (i.e., CNC, milling) to adjust a geometrical shape of the orthopedic orthoses 304, 504, 604, 704, 804 after production to tighten or enlarge a fit of the orthopedic orthoses 304, 504, 604, 704, 804.

The blanks 302, 502, 602, 702, 802 and/or blocks 303, 503, 603, 1001, 1002, 1003, 1004 may include external features and attachment mechanisms, such as the latching mechanisms 1100a, 1100b thereon prior to manipulation with the CNC machine 300.

The orthopedic orthoses 304, 504, 604, 704, 804 may be configured for alteration by placing the orthopedic orthoses 304, 504, 604, 704, 804 back into the subtractive manufacturing machine or CNC machine 300 after an initial machining process for positioning or adding a clamp/marker that can be further altered. The orthopedic orthoses 304, 504, 604, 704, 804 may be altered by placing the orthopedic orthoses 304, 504, 604, 704, 804 back into the CNC machine 300 after 3D scanning the orthopedic orthoses 304, 504, 604, 704, 804 following an initial machining process and a 3D printed positioning jig is produced to re-calibrate the orthopedic orthoses 304, 504, 604, 704, 804 for further modification by the subtractive CNC machine 300.

A special adaption may be incorporated or milled into the orthopedic orthoses 304, 504, 604, 704, 804 to allow for receipt of a bridge (premanufactured) piece which may be made of elastic material to provide a modular component, adaptive design or swelling zone to the orthopedic orthoses 304, 504, 604, 704, 804.

The housing 106 is configured to support the sensor 102, the light source 101, the holder 103, the checkerboard 104, the central processor 105, the monitor 105a and other portions of the system associated with the 3D scanner 100. The sensor 102 may be configured to scan and collect images of the body part 107 and to send commands and process data in the preferred embodiment. In the preferred embodiment, the housing 106 is a mechanical structure in the shape of an open box to fix the sensor 102, the uniform light source 101, the holder 103, the checkerboard 104, the central processor 105 and the monitor 105a. The mechanical structure or housing 106 is configured to receive the body part 107 or other object therein for scanning. The housing 106 is not limited to the open box configuration and may be designed and configured to have nearly any size and shape that is able to accept the body part 107 for scanning and to perform the additional functions of the housing 106 described herein. The housing 106 may support the sensor 102 and the light source 101 therein in single or multiple arrays depending on design preferences or application particularities.

The central processor 105 may be configured to develop optimization of 3D manufacturing parameters, mechanical properties prediction, mesh post-processing, and use the data for orthopedic applications such as designing the orthopedic orthoses 304, 504, 604, 704, 804 described herein. The central processor 105 may be in communication with an electronic medical record ("EMR") of the patient and perform optical character recognition ("OCR") of the patient's electronic medical record to assist in defining the 3D model and the CNC programming file.

The sensor 102 may scan a texture of the body part 107 and the central processor 105 preferably includes an algorithm that reconstructs the orthopedic orthoses 304, 504, 604, 704, 804 automatically based on a prescribed size, marked outlines on the patient limb, application, features such as deformities, ulcers, sores, wounds, and related features automatically or manually.

The central processor 105 may include a deformation algorithm that corrects the 3D model, wherein the 3D model is configured as a hand/foot or any scanned limb or body part 107. The central processor 105 may correct the 3D model automatically or manually to a required anatomical position for casting, splinting, and any orthoses.

The preferred process may include the steps of: 1) making the pre-made mold, 2) customizing the pre-made mold, 3) remove the support, and 4) capturing the output product. The preferred subtractive technology manipulates the blanks 302, 502, 602, 702, 802 and/or blocks 303, 503, 603, 1001, 1002, 1003, 1004 based on the customized orthotic shape (3D Cast) of the 3D model.

The mold inventory 900 may include thicker cylindrical pre-made blanks 302, 502, 602, 702, 802 and/or blocks 303, 503, 603, 1001, 1002, 1003, 1004, wherein the process to be utilized by the subtractive technology to generate the orthopedic orthoses 304, 504, 604, 704, 804.

It will be appreciated by those skilled in the art that changes could be made to the embodiments described above without departing from the broad inventive concept thereof. As a non-limiting example, artificial intelligence ("AI") can be utilized to adjust the position of the arm/hand/limb of the patient using augmented reality ("AR"), virtual reality ("VR"), or AI can be used to model the hand and give visual feedback to the prescribed (doctor or practitioner using AR or VR), particularly when positioning the body part 107 on the holder 103. It is understood, therefore, that this invention is not limited to the embodiments disclosed, but it is intended to cover modifications within the spirit and scope of the present invention as defined by the present description.

We claim:

1. A three-dimensional subtractive manufacturing system configured for constructing an orthopedic orthosis from a first blank and a second blank of a plurality of blanks, the system comprising:

a scanner configured to capture a three-dimensional model of a body part of a patient, the scanner including a light source configured to illuminate the body part and a sensor to capture images of the body part;

a central processor configured to receive the three-dimensional model and select the first and second blanks based on the three-dimensional model, the central processor configured to convert the three-dimensional model into a computer numeric control programming file, the central processor includes an inventory management processing unit, the inventory management processing unit configured to optimize the computer numeric control programming file and production time of the orthopedic orthosis by selection of the first blank and machining parameters implementation in the computer numeric control programming file; and a computer numerical control machine configured to receive the computer numeric control programming file and an identification of the first and second blanks from the central processor, the computer numerical control machine comprised of a subtractive manufacturing machine, the computer numerical control machine configured to remove material from the first and second blanks to define first and second orthoses, the first orthosis secured to the second orthosis to form the orthopedic orthosis.

2. The three-dimensional subtractive manufacturing system of claim 1, further comprising:

a post processing unit to remove a support from the orthopedic orthosis and to surface treat the orthopedic orthosis.

3. The system of claim 1, wherein the body part includes an arm, a wrist, a leg, a hand, a knee and an ankle, the plurality of blanks includes arm blanks, wrist blanks, leg blanks, hand blanks, knee blanks, ankle blanks and additional blanks.

4. The system of claim 1, wherein the central processor includes an automatic modeling software, the automatic modeling software creates the three-dimensional model to select the first blank, the automatic modeling software configured such that if the plurality of blanks does not include the first blank or an irregular shape of the body part is detected, the central processor suggests an additive manufacturing process.

5. The system of claim 1, wherein the plurality of blanks includes multiple sized blanks that have overlap for the body part, the orthopedic orthosis constructed from the first blank and a second blank that are machined for combination.

6. The system of claim 5, wherein the first and second blanks are connected with a latching mechanism.

7. The system of claim 1, wherein the first blank has a pre-bent shape conforming generally to the body part.

8. The system of claim 1, wherein the first blank includes a ninety degree portion, the ninety degree portion configured to accommodate an ulnar gutter where a hand meets a patient's fingers.

9. The system of claim 1, wherein the first blank has a multicolor or patterned appearance.

10. The system of claim 1, wherein the first blank includes holes and patterns prefabricated thereon.

11. The system of claim 1, wherein each of the plurality of blanks is constructed by injection molding or additive manufacturing of a polymeric material, the computer numerical control machine configured for subtractive manufacturing of the first blank to define the orthopedic orthosis.

12. A three-dimensional subtractive manufacturing system configured for constructing an orthopedic orthosis from a first blank and a second blank of a plurality of blanks, the system comprising:

a scanner configured to capture a three-dimensional model of a body part of a patient, the scanner including a light source configured to illuminate the body part and a sensor to capture images of the body part;

a central processor configured to receive the three-dimensional model and select the first and second blanks based on the three-dimensional model, the central processor configured to convert the three-dimensional model into a computer numeric control programming file; and a computer numerical control machine configured to receive the computer numeric control programming file and an identification of the first and second blanks from the central processor, the computer numerical control machine comprised of a subtractive manufacturing machine, the computer numerical control machine configured to remove material from the first and second blanks to define first and second orthoses, the first orthosis secured to the second orthosis to form the orthopedic orthosis, wherein the central processor is configured to track used blanks of the plurality of blanks based on the identification of the first blank and any additional blanks of the plurality of blanks, predict needs for replenishment of the plurality of blanks, and analyze patterns of the used blanks for inventory optimization.

* * * * *